United States Patent [19]

Kataoka et al.

[11] Patent Number: 5,393,915

[45] Date of Patent: Feb. 28, 1995

[54] METHOD OF PREPARING α-L-ASPARTYL-L-PHENYLALANINE METHYL ESTER OR ITS HYDROCHLORIDE SALT

[75] Inventors: Takehiko Kataoka; Akihiko Yasaki; Shinichi Kishimoto; Toshihisa Kato, all of Kawasaki, Japan

[73] Assignee: Ajinomoto Co., Inc., Tokyo, Japan

[21] Appl. No.: 153,490

[22] Filed: Nov. 17, 1993

Related U.S. Application Data

[63] Continuation of Ser. No. 888,628, May 27, 1992, abandoned.

[30] Foreign Application Priority Data

May 31, 1991 [JP] Japan ................................. 3-229827
May 31, 1991 [JP] Japan ................................. 3-229828
Apr. 14, 1992 [JP] Japan ................................. 4-094203

[51] Int. Cl.⁶ .......................................... C07C 229/34
[52] U.S. Cl. .......................................... 560/41
[58] Field of Search .................................. 560/41

[56] References Cited

U.S. PATENT DOCUMENTS 3,943,233  3/1976  Swanson et al. ...................... 423/332
4,618,695  10/1986  Ozawa et al. ........................ 560/41
4,918,216  4/1990  Mita et al. ........................... 560/41

OTHER PUBLICATIONS

"Chemical Engineers' Handbook", Robert H. Perry Cecil H. Chilton, 5th Edition; 19-80; 1973.

Horizontal Belt Filters In Wet-Process Phosphoric Acid Plants; R. J. B. McNally et al. 1978 Proc. Annu. Meet-Fert. Ind. Round Table.

Utilization of Horizontal Belt Filters for Washing Fine Alumina Seed and Kiln Feed Product Richard Crawford: Donald A. Dahlstrom Light Met. 1984.

Chemical Abstracts, 159814h, vol. 115, No. 15, Oct. 14, 1991, & JP-A-3 106 899, May 7, 1991, p. 1008, T. Harada, et al., "Crystallization of Alpha-L-Aspartyl-L-Phenylalanine Methyl Ester".

Chemical Abstracts, 56620t, vol. 108, No. 7, Nov. 15, 1988, & JP-A-62 153 298, Jul. 8, 1987, p. 780, Y. Miyaki, et al., "A Method for the Purification of Aspartame by Dialysis".

M. P. Deutscher, "Guide to Protein Purification", 1990, pp. 67-68.

*Primary Examiner*—José G. Dees
*Assistant Examiner*—Samuel Barts
*Attorney, Agent, or Firm*—Oblon, Spivak, McClelland, Maier & Neustadt

[57] ABSTRACT

A method for the solid-liquid separation of a suspension of α-L-aspartyl-L-phenylalanine methyl ester (α-APM) or its hydrochloride salt (α-APM.HCl), wherein an aqueous suspension of α-L-aspartyl-L-phenylalanine methyl ester or its hydrochloride salt is subjected to continuous separation by vacuum filtration.

15 Claims, No Drawings

METHOD OF PREPARING α-L-ASPARTYL-L-PHENYLALANINE METHYL ESTER OR ITS HYDROCHLORIDE SALT

This application is a continuation of application Ser. No. 07/888,628, filed on May 27, 1992, now abandoned.

BACKGROUND OF THE INVENTION

1. Field of the Invention

The present invention relates to methods of preparing α-L-aspartyl-L-phenylalanine methyl ester (hereinafter referred to as "α-APM") or its hydrochloride salt (hereinafter referred to as "α-APM.HCl"). More particularly, it relates to methods of preparing α-APM or α-APM.HCl by solid-liquid separation of an aqueous suspension of the salt.

2. Discussion of the Background

α-APM is a low-calorie dipeptide diet sweetener having a sweetness which is about 200 times that of sucrose (cane sugar). It is expected that the world demand for this product will exceed 10,000 tons before 1995. The hydrochloride salt of α-APM, α-APM.HCl, is an important intermediate for the preparation of α-APM.

The following methods are examples of known industrial methods for the production of α-APM:

(1) a method of obtaining α-APM wherein an N-protected aspartic acid anhydride and a phenylalanine methyl ester are condensed in an organic solvent and the protective group is removed from the product (see U.S. Pat. No. 3,786,039 incorporated herein by reference);

(2) a method of obtaining α-APM in which α-L-aspartyl-L-phenylalanine is methyl-esterified in a mixed solvent comprising water, methanol and hydrochloric acid, to obtain α-APM.HCl, which is then neutralized to obtain α-APM (see Japanese Patent Application Laid-Open No. 53-82752); and (3) a method of obtaining α-APM in which an N-protected aspartic acid anhydride and a phenylalanine methyl ester are condensed in the presence of an enzyme, and the protective group is subsequently removed from the product (see Japanese Patent Publication No. 55-135595).

In above synthetic method (1), the β-isomer (i.e., β-L-aspartyl-L-phenylalanine methyl ester (β-APM)) is produced as a side product. As a means for selectively removing impurities, including this β-isomer, there is known a purification method (4) in which an α-APM product containing impurities is brought into contact with a hydrohalogenic acid and then subjected to solid-liquid separation so as to isolate α-APM as its hydrohalide salt.

When considering the industrial scale production of α-APM to meet the trend of present consumption demands, chemical methods are presently favored from the viewpoint of manufacturing cost. In such cases, esterification of the product is often achieved via its hydrochloride salt as in above method (2), or after formation of α-APM, the α-APM is often made into its hydrohalide salt (α-APM.Hal), such as hydrochloride salt to purify it as in above method (4).

To obtain α-APM from its hydrohalide salt, such as its hydrochloride salt, the α-APM.Hal is dissolved or suspended in an aqueous medium and the resulting solution or suspension neutralized through the addition of a base. This is followed by cooling the neutralized liquid to yield a suspension of α-APM. The resulting suspension of α-APM is then subjected to solid-liquid separation. In general, a centrifugal separator is used for such solid-liquid separation When α-APM.HCl, which is a useful intermediate in the preparation of α-APM, is separated by a method such as above methods (2) or (4), there is a high probability of product contamination by undesirable by-products. In above method (4), after removal of the protective group, the reaction mixture still contains various impurities such as β-APM, in addition to α-APM. In above method (2), the α-L-aspartyl-L-phenylalanine (α-AP) used as the starting material for methyl-esterification, most often contains impurities, such as β-APM as a by-product from the previous step. In these cases, however, a high-purity α-APM.HCl product can be obtained by selectively precipitating α-APM.HCl on the basis of its difference in solubility, followed by solid-liquid separation of the suspension. For such solid-liquid separation, in general, a centrifugal separator is used.

For separating a suspension of α-APM and α-APM.HCl, the mother liquor which remains adhered to the cake must be removed by washing the cake. As the washing procedure, substitution washing is suitable because of its simplicity. However, where separation of the suspension is performed with a centrifugal separator, as is generally done, there is the significant problem that the amount of washing liquid necessary for the washing is fairly large.

When one considers (a) the large amount of impurities which can be present in the mother liquor, (b) the high purity required of α-APM as a commercial product and (c) the role of the α-APM.HCl as an intermediate for preparing α-APM, the α-APM and α-APM.HCl crystals have to be washed to a level sufficient to achieve the highest purity attainable. However, when the amount of washing liquid is increased, not only does the cost of the process increase because of the increased cost of the washing liquid, but there is also necessarily a decrease in product yield due to increasing loss of α-APM or its hydrochloride salt and other valuable compounds from the cake due to their dissolution into the washing liquid. Even when recovery of product dissolved in the washing liquid is taken into consideration, the operation is very costly and difficult because of the large amounts of liquid processed and the low concentration of compounds dissolved therein.

Where a centrifugal separator is used and it is desired to increase the degree of dehydration, the separating operation must be effected in a batchwise manner. If the feeding of liquid, separation, washing, dehydration, and the removal of the cake are carried out as a series of operations, there is the additional problem that the requisite processing plant must be large-scaled.

In addition, the operation itself is also complicated. Besides the complication of having to carry out the separation several times, there is another problem in that the cake which adheres to the filter cloth must be scraped off by hand. This additional process step requires an increase in the amount of labor (number of workers) needed for the operation, and the time and number of steps required for processing increase, resulting in overall increased cost and overall decreased yield. In light of the considerable commercial demand for α-APM there is a clear need for notably improved processes free of the above disadvantages.

SUMMARY OF THE INVENTION

The present invention has overcome the problems encountered in the methods of the prior art including but not limited to: (1) the large amount of washing liquid necessary for washing the cake in solid-liquid separation of the suspension of α-APM or its hydrochloride salt, (2) that the operation is carried out batchwise requires a large-scaled equipment plant, and (3) that the operation is complicated requiring a large number of necessary workers in charge of the operation.

The objects of the present invention include: (1) decreasing the amount of washing liquid necessary for washing the crystal cake in solid-liquid separation of the suspension of the α-APM or its hydrochloride salt, (2) providing an industrial operation which does not need to be carried out batchwise thereby eliminating the need for a large-scale equipment plant, (3) simplification of the operation thereby eliminating the need for a large number of workers in charge of the operation, and (4) increasing the overall efficiency of the method for isolation of α-APM or its hydrochloride salt, thereby reducing the overall cost of preparation while increasing the overall yield of product.

The present invention, which is particularly useful in the industrial-scale production of α-APM and/or α-APM.HCl, involves subjecting an aqueous suspension of α-APM or its hydrochloride salt to solid-liquid separation by vacuum filtration to produce α-APM or its hydrochloride salt in an industrial scale operation, wherein the washing efficiency of washing the cake is extremely improved and additionally the operation may be carried out continuously. Therefore, the amount of plant equipment needed may be reduced, and the maintenance operation of scraping the cake simplified. Further, the invention allows for a reduction in the number of workers necessary for operation of the process. As a result, the invention provides an industrially very valuable method.

DETAILED DESCRIPTION OF THE PREFERRED EMBODIMENTS

The present inventors made earnest and repeated investigations for the purpose of overcoming the above-mentioned problems in solid-liquid separation of a suspension of α-APM or its hydrochloride salt and, as a result, have found the following novel methods.

More particularly, their finding is that if a separation of a suspension of α-APM or its hydrochloride salt is effected by vacuum filtration in such a way that the pressure on the side of the filtrate from the filter cloth is reduced, the amount of washing liquid necessary to wash the cake is surprisingly substantially reduced, and as a result, the above-mentioned cost and loss may be reduced.

In addition, it has also been found that continuous separation of the suspension with a high dehydrating degree may be effected by vacuum filtration so that the amount and/or size of necessary plant equipment may be reduced as compared with the batchwise separation and the whole operation for the separation may be simplified while allowing for an improved yield of product having higher purity.

The present inventors have applied these findings to the actual process of producing α-APM or its hydrochloride salt, whereby they have overcome the above-mentioned problems. The present invention allows for the production of α-APM or its hydrochloride salt with a reduction of the necessary plant equipment and the number of workers needed for the production process.

Specifically, the present invention relates to a method of preparing α-APM or its hydrochloride salt by solid-liquid separation of an aqueous suspension of α-APM or its hydrochloride salt, which is characterized in that the aqueous suspension is subjected to continuous separation by vacuum filtration.

The separator to be used in the present invention may be any known separator which can be used for continuous vacuum filtration. In view of the ease of scraping the formed cake and the applicability of countercurrent multi-stage washing thereto, a horizontal belt type filter is preferred.

When using a horizontal belt type filter, the thickness of the wet crystal cake should not be too large. When this occurs the liquid-solid separation decreases and as a result the degree of dehydration as well as the washability of the cake also decrease. Alternately, if the thickness of the cake is too thin, another problem arises in that the degree of vacuum becomes low and it becomes difficult to separate the cake from the belt.

The optimum thickness for any given cake differs slightly according to the properties of particular cake. For example, in the case of an α-APM wet cake obtained by neutralizing α-APM.HCl with base followed by cooling, crystallizing and separating α-APM, the cake thickness should be in the range of from 3 mm to 20 mm, preferably from 5 mm to 15 mm. In the case of an α-APM wet cake obtained by cooling crystallization of the heat-condensed mother liquor formed after crystallizing and separating the α-APM, the thickness should be in the range of from 2 mm to 15 mm, preferably from 3 mm to 10 mm. In the case of an α-APM.HCl wet cake, cake thickness should be in the range of from 5 mm to 30 mm, preferably from 10 mm to 20 mm.

The thickness of the wet cake can be adjusted by changing the feeding speed of the aqueous suspension to the filter and the running speed of the filter belt. Before making any adjustment it is desirable to calculate the concentration of the slurry. However it is easy for the person skilled in the art to adjust to the optimum condition by simple empirical test.

The level of vacuum is about −200 to about −700 mm Hg (the filtration pressure differential is about 200 to about 700 mm Hg). Preferably the level of vacuum is about −300 to about −700 mm Hg, more preferably it is about −400 to about −600 mm Hg.

In accordance with the invention, the amount of washing liquid used for washing wet crystals of α-APM obtained by separation of the suspension, is suitably not more than two times the weight of the wet crystals to be washed therewith, thereby reducing the above-mentioned cost and product loss due to dissolution. The washing liquid to be used may be water. But, if α-APM or its derivatives are soluble in the washing liquid, loss of α-APM crystals increases thereby decreasing product yield, or undesirable channels may form in the cake, lowering washing efficiency. Therefore, an aqueous solution of α-APM can be advantageously used as the washing liquid of α-APM wet crystals, thereby decreasing the probability of dissolution of soluble products.

Also, in the case of wet crystals of α-APM.HCl, the amount of washing liquid to be used for washing wet crystals obtained by separation of the suspension is suitably the same weight as or less than the weight of the wet crystals to be washed. The washing liquid to be used may be water. However, if α-APM or its hydrochloride salt dissolves out from the wet crystals cake into the washing liquid, loss of crystals increases resulting in decreased yield, or the formation of undesirable channels in the cake which lower washing efficiency. Therefore, aqueous hydrochloric acid or an aqueous solution of α-APM or its hydrochloride salt can be used as the washing liquid thereby decreasing the probability of dissolution of the soluble products.

Other features of the invention will become apparent in the course of the following descriptions of exemplary embodiments which are given for illustration of the invention and are not intended to be limiting thereof.

EXAMPLES

Example 1: (300-ml scale experiment)

300 ml of an aqueous suspension of α-APM containing 1.5 wt. % of dissolved NaCl (slurry concentration 3.3 wt. %; liquid temperature 5° C.) was filtered with a top-feed system suction filter (leaf tester, filtration area 0.0063 $m^2$). The filtration pressure difference was 400 mmHg. After dehydrating for 30 seconds, 36 g of cake having a water content of 69 wt. % was obtained. The thickness of the cake was 8 mm.

Next, using the same apparatus, 300 ml of the same slurry was filtered under the same condition. Thereafter, the cake was washed by pouring 50 g of a saturated aqueous α-APM solution (corresponding to 1.4 times the weight of the cake) over the cake while maintaining reduced pressure on the side of the filtrate. After washing, the NaCl content in the cake was found to be about 1% of that in the unwashed cake. Thus, 99% of the NaCl in the unwashed cake was removed by the washing operation.

Example 2: (one-$m^3$ scale experiment)

The same aqueous α-APM suspension as that used in Example 1 was continuously filtered with a horizontal belt type vacuum filter (Tsukishima Panebisu Horizontal Belt Filter, manufactured by Tsukishima Machinery Co.; filtration area 3.5 $m^2$). The amount of aqueous suspension fed to the filter was 3.2 $m^3$/hr, the filtration difference pressure was 400 mmHg, and the belt speed was about 1.5 m/min. The amount of the cake obtained was 0.40 ton/hr. The thickness of the cake was 8 mm. The water content in the cake was 70 wt. %.

Next, one-stage washing of the cake was effected continuously with 0.40 ton/hr of a saturated aqueous α-APM solution (almost the same amount as that of the cake) during the filtration, and the NaCl content in the washed cake decreased to 2% of that in the unwashed cake. Thus, 98% of NaCl in the unwashed cakes was removed by the washing operation.

The continuous operation was carried out for 50 hours, whereupon 160 $m^3$ in total, or 22 $m^3$/day.$m^2$ (unit filtration area) of the suspension was treated (filtered). The peelability of the cake from the filter cloth was good and the scraping of cake adhered to the filter cloth could easily be effected without necessity of manual operation.

Example 3: (300-ml scale experiment)

300 ml of an aqueous suspension of α-APM (slurry concentration 2.6 wt. %; dissolved NaCl concentration 5.0 wt. %; liquid temperature 5° C.), obtained by heating and concentrating the filtrate obtained in Example 2 to 1/5.5 (vol./vol.) followed by again subjecting the concentrated filtrate to cooling crystallization, was filtered with the same apparatus as used in Example 1. The filtration pressure difference was 400 mmHg. After dehydrating for 30 seconds, 34 g of cake having a water content of 75 wt. % was obtained. The thickness of the cake was 6 mm.

Next, using the same apparatus, 300 ml of the same slurry was filtered under the same conditions. Thereafter, 37 g of a saturated aqueous α-APM solution (corresponding to 1.1 times the weight of the cake) was poured over the cake so as to wash them, with maintaining a reduced pressure on the side of the filtrate. After washing, the NaCl content in the cake was found to be about 25% of that in the unwashed cake. Thus, 75% of the NaCl in the unwashed cake was removed by the washing operation.

Example 4: (1-$m^3$ scale experiment)

The same aqueous α-APM suspension as that used in Example 3 was continuously filtered with the same filter apparatus as used in Example 2. The amount of the aqueous suspension as fed to the filter was 1.0 $m^3$/hr, the filtration pressure difference was 400 mmHg, and the belt speed was about 0.6 m/min. The amount of the cake obtained was 0.11 ton/hr. The thickness of the cake was 6 mm. The water content in the cake was 74 wt. %.

Next, one-stage washing of the cake was effected continuously with 0.17 ton/hr of an aqueous saturated α-APM solution (1.5 times the weight of the cake) during the filtration, and the NaCl content in the washed cake decreased to 10% of that in the unwashed cake. Thus, 90% of NaCl in the unwashed cake was removed therefrom by washing.

Comparative Example 1: (1-$m^3$ scale experiment)

The same suspension as used in Example 1 was filtered with a bottom-discharging centrifugal separator (basket diameter 1220 mm × depth 410 mm; filtration area 1.5 $m^2$). After 0.8 $m^3$ of the suspension was filtered, 90 kg of cake having a water content of 66 wt. % was obtained. The cake had a thickness of about 60 mm.

Next, using the same apparatus, 0.8 $m^3$ of the same suspension was filtered under the same condition, and thereafter 180 kg of an aqueous saturated α-APM solution, which was 2.0 times the weight of the cakes, was added to the cake to wash same. As a result, the water content in the cake obtained was 60 wt. % and the NaCl content decreased to only 42% of that in the unwashed cake.

The time spent for the batchwise operation (feeding of the suspension, dehydrating, feeding of the washing solution, dehydrating, and discharging of cakes) was 3 hours on the average. Due to the increase in operation time because the cake located between the scratching blades and the filter cloth became consolidated, a cake peeling operation was needed in 1 out of every 7 operations. The time spent for each operation was 1.5 hours. The amount of suspension which could be treated per the unit filtration area per day using this operation was calculated to be 4.0 $m^3$/day.$m^2$, which was found to be only about one sixth of the amount treated in Example 2.

Example 5: (300-ml scale experiment)

300 ml of an aqueous suspension of α-APM.HCl (slurry concentration 12.4 wt. %; liquid temperature 10° C.) was filtered with a top-feed system suction filter (leaf tester, filtration area 0.0093 $m^2$). The filtration pressure difference was 400 mmHg. After dehydrating for 10 seconds, 64 g of cake having a water content of 35 wt. % was obtained. The thickness of the cake was 12 mm and the cake contained 1.6 wt. % of β-AP.

Next, using the same apparatus, 300 ml of the same slurry was filtered under the same condition. Thereafter, 60 g of 2N aqueous hydrochloric acid was poured over the cake to wash it, maintaining a reduced pressure on the filtrate side of the filtration. After washing, the water content in the cake was 35 wt. %, and the β-AP content 0.1 wt. % or less.

Example 6: (100-liter scale experiment)

An aqueous suspension of α-APM hydrochloride (slurry concentration 22.2 wt. %; liquid temperature 10° C.) was continuously filtered with a horizontal belt type vacuum filter (Tsukishima Panebisu Horizontal Belt Filter, manufactured by Tsukishima Machinery Co.; filtration area 0.8 m²). The amount of aqueous suspension fed to the filter was 260 liter/hr, the filtration pressure difference was 400 mmHg, and the belt speed was about 1 m/min. The amount of the cake obtained was 100 kg/hr. The water content in the cake was 30 wt.%, the β-AP content was 14 wt %. The thickness of the cake was in the range of from 12 mm to 13 mm.

Next, one-stage washing of the cake was effected continuously with 100 kg/hr of 2N aqueous hydrochloric acid during the filtration. The water content of the cake obtained was 30 wt. %, the β-AP content was 0.1 wt. % or less.

The continuous operation was carried out for 24 hours, whereupon 6200 liter or 7800 liter/day.m² of the suspension was treated (filtered) as a whole. The peelability of the cake from the filter cloth was good and scraping of cake adhered to the filter cloth could easily be achieved without manual operation.

Comparative Example 2: (50-liter scale experiment)

The same suspension as used in Example 6 was filtered with a top-discharging centrifugal separator (basket diameter 658 mm × depth 295 mm; filtration area 0.6 m²). After 70 liters of the suspension was filtered, 29 kg of cake having a water content of 32 wt. % were obtained. The cake had a β-AP content of 2.0 wt. %.

Next, using the same apparatus, 70 liters of the same suspension was filtered under the same condition, and thereafter 45 kg of 2N aqueous hydrochloric acid, which was 1.5 times the weight of the cake, was added to the cake to wash it. As a result, the water content in the cake obtained was 30 wt % the β-AP content was only lowered to 0.5 wt. %.

The time spent for the batchwise operation (feeding of the suspension, dehydrating, feeding of the washing solution, dehydrating, and discharging of cakes) was 90 minutes, and this time did not change even after 6 times of operation and after the operator became skilled in the operation. On the basis of these values, the amount of the suspension which could be treated per unit filtration area per day was calculated to be 1800 liter/day m² which was found to be only about 1/4.3 of the amount achieved in Example 6.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for isolating α-L-aspartyl-L-phenylalanine methyl ester or its hydrochloride salt from an industrial-scale aqueous suspension of the same, comprising subjecting said aqueous suspension to continuous separation by vacuum filtration.

2. The method of claim 1, wherein said continuous separation is performed with a horizontal belt-type filter.

3. The method of claim 1, comprising subjecting to said continuous separation by vacuum filtration, as said aqueous suspension of α-L-aspartyl-L-phenylalanine methyl ester, an acid-addition salt of α-L-aspartyl-L-phenylalanine methyl ester neutralized with a base, followed by subjecting the neutralized product to cooling crystallization.

4. The method of claim 2, comprising subjecting to said continuous vacuum filtration, as said α-L-aspartyl-L-phenylalanine methyl ester, an acid-addition salt of α-L-aspartyl-L-phenylalanine methyl ester neutralized with a base, followed by subjecting the neutralized product to cooling crystallization.

5. The method of claim 3, comprising obtaining a cake of wet crystals of α-L-aspartyl-L-phenylalanine methyl ester having a thickness in a range of from 3 mm to 20 mm, after said continuous separation by vacuum filtration.

6. The method of claim 1, wherein said aqueous suspension of α-L-aspartyl-L-phenylalanine methyl ester is obtained by cooling crystallization of a heat-condensed mother liquor formed after crystallizing and separating said α-L-aspartyl-L-phenylalanine methyl ester.

7. The method of claim 6, wherein a cake of wet crystals of α-L-aspartyl-L-phenylalanine methyl ester having a thickness of from 2 mm to 15 mm is obtained.

8. The method of claim 3, wherein said crystals obtained by said continuous separation by vacuum filtration of said aqueous suspension are continuously washed with a washing liquid in an amount not greater than two times the weight of said wet crystals.

9. The method as claimed in claim 8 wherein said washing liquid is one member selected from the group consisting of water and aqueous solutions of α-L-aspartyl-L-phenylalanine methyl ester.

10. The method of claim 1, wherein a cake of wet crystals of α-L-aspartyl-L-phenylalanine methyl ester hydrochloride having a thickness of from 5 mm to 30 mm is obtained from said continuous separation by vacuum filtration.

11. The method of claim 1, wherein wet crystals of α-L-aspartyl-L-phenylalanine methyl ester hydrochloride obtained by said continuous separation by vacuum filtration of said aqueous suspension are continuously washed with a washing liquid in an amount not greater than the weight of said wet crystals.

12. The method of claim 11 wherein said washing liquid is a member selected from the group consisting of water, aqueous hydrochloric acid, and aqueous solutions of α-L-aspartyl-L-phenylalanine methyl ester or α-L-aspartyl-L-phenyl methyl ester hydrochloride.

13. The method of claim 2, wherein wet crystals obtained by separating said aqueous suspension are continuously washed with a washing liquid in an amount not greater than two times the weight of said wet crystals.

14. The method of claim 13, comprising using counter-current washing.

15. The method of claim 6, wherein said crystals obtained by said continuous separation by vacuum filtration of said aqueous suspension are continuously washed with a washing liquid in an amount not greater than two times the weight of said wet crystals.

* * * * *